United States Patent [19]

Brookfield

[11] Patent Number: 5,503,003
[45] Date of Patent: Apr. 2, 1996

[54] PORTABLE VISCOMETER

[75] Inventor: David A. Brookfield, Sharon, Mass.

[73] Assignee: Brookfield Engineering Laboratories, Inc., Stoughton, Mass.

[21] Appl. No.: 355,634

[22] Filed: Dec. 14, 1994

[51] Int. Cl.⁶ .................................................. G01N 11/14
[52] U.S. Cl. ........................................ 73/54.32; 73/54.28
[58] Field of Search ............................... 73/54.01, 54.14, 73/54.16, 54.28, 54.31, 54.32, 54.33, 54.34, 54.37, 54.43

[56] References Cited

U.S. PATENT DOCUMENTS

| | | | |
|---|---|---|---|
| 2,027,903 | 1/1936 | Dintilhac | 73/54.28 |
| 2,553,844 | 5/1951 | Buchdahl et al. | 73/54.28 |
| 2,643,543 | 6/1953 | Herzog | 73/54.34 |
| 2,660,885 | 12/1953 | Evans | 73/54.28 |
| 3,435,666 | 4/1969 | Fann | 73/54.39 |
| 3,886,789 | 6/1975 | Brookfield | 73/59 |
| 4,175,425 | 11/1979 | Brookfield | 73/59 |
| 4,448,061 | 5/1984 | Brookfield | 73/59 |
| 4,571,988 | 2/1986 | Murphy | 73/54.33 |
| 5,167,143 | 12/1992 | Brookfield | 73/54.23 |

OTHER PUBLICATIONS

Title: Apparatus for Studying the Rheological Behavior of Carbonaceous Materials at Elevated Temperature and Pressure Authors: Garratt, G. W.; Rand, B.; Whitehouse, S. Source: Fuel V 67 N 2 Feb. 1988 P 238–241.

*Primary Examiner*—Hezron E. Williams
*Assistant Examiner*—Jay L. Politzer
*Attorney, Agent, or Firm*—Jerry Cohen; Harvey Kaye

[57] ABSTRACT

Viscometer with a spindle (4) mounted on a shaft (8) supported via axially spaced, e.g. three inches, bearings (12,14) and driving a transducer rotary member via a stiff rotationally resilient member, the latter providing substantially all the resistive torque to viscous drag imparted to the spindle by an outer driven rotating member (6) when the spindle and rotating member are immersed in a liquid whose viscosity is to be measured, the viscometer being constructed with a handle (38) that encloses motor drive and electronic components of the viscometer, these features, as a whole, providing explosion protection and portability of the viscometer with sensitivity appropriate to portable usage.

8 Claims, 2 Drawing Sheets

PORTABLE VISCOMETER

FIELD OF THE INVENTION

The field of the present invention relates to viscometers and more particularly to variable speed viscometers packaged in explosion proof housing with continuous readouts.

BACKGROUND OF THE INVENTION

Viscometers of the type disclosed in U.S. Pat. No. 4,448,061 (May 15, 1984) of David A. Brookfield, of common assignment with the present invention, drive a cup within a housing with a liquid between the cup and the housing whose viscosity is to be measured. The liquid's viscosity retards the movement of the cup. In such viscometers a resilient connection is included in the shaft driving the cup. The deflection of this resilient connection is a measure of the drag provided by the liquid's viscosity, and the deflection is measured and may be calibrated to read the viscosity directly, see the above referenced U.S. patent and the referenced therein.

A liquid between two surfaces will shear when one surface moves relative to the other. The force needed to make such a movement is directly related to the viscosity of the liquid (with the mechanical configuration factored out). Viscometers typically rotate a cup or bob within a cylinder with the liquid therebetween, or rotate a cone relative to a plate with the liquid therebetween. In such examples, torque is directly related to the viscosity of the liquid (again with mechanical configuration factored out). The present state of the art, besides measuring torque, also includes measuring time to torque, either of which may be calibrated to read viscosity.

It is known in the art to provide a spring connection between two slotted wheels, where one wheel is attached to a mechanism that is sensitive to the drag caused by a viscous liquid, and the other wheel is attached to a mechanical drive assembly. When operated, the wheel sensitive to drag deflects with respect to the driven wheel. Optical sensors detect the slots and the resulting deflection is measured as a time delay offset between the reading of the optical sensors that is calibrated to indicate the viscosity of the liquid.

It is an object of the present invention to provide a rugged, portable viscometer with integrated electronics.

It is another object to provide a viscometer package within a housing that is explosion proof.

It is another object to provide a viscometer that operates with a wide range of liquids and over a wide range of temperatures and environments.

It is another object of the invention to provide a viscometer that is inexpensive to manufacture yet meets industry standards of accuracy, reliability, durability, dependability, and ease of maintenance and cleaning.

SUMMARY OF THE INVENTION

The above objects are met in an apparatus including a fixed housing with an extended cylindrical chamber, a rotatable cylindrical structure coaxially mounted within the chamber, where the space between the chamber and the structure defines a volume filled with a liquid being measured, a first drive shaft, coaxial with said cylindrical chamber, with an end fixed to said cylindrical structure, a variable speed motor driving a second drive shaft, a resilient member joining the first drive shaft and the second drive shaft, said resilient member deflecting responsive to the drag of said liquid sheared between the chamber and the rotating cylindrical structure, and means for continuously reading the deflection and calibrating said reading into viscosity. The viscosity measuring zone is extended well beyond the housing (for example 17 inches with 3 inch axial separation of the rigid radial support shaft bearings) via a thick, rigid shaft to control the measurement annulus and provide ruggedness for the probable abuse that a portable viscometer will undergo.

The objects are met in an explosion proof housing system which meets all requirements and including low cost pickups including low cost to manufacture.

Other objects, features and advantages will be apparent from the following detailed description of preferred embodiments taken in conjunction with the accompanying drawings in which:

BRIEF DESCRIPTION OF PREFERRED EMBODIMENTS

Figure 1:
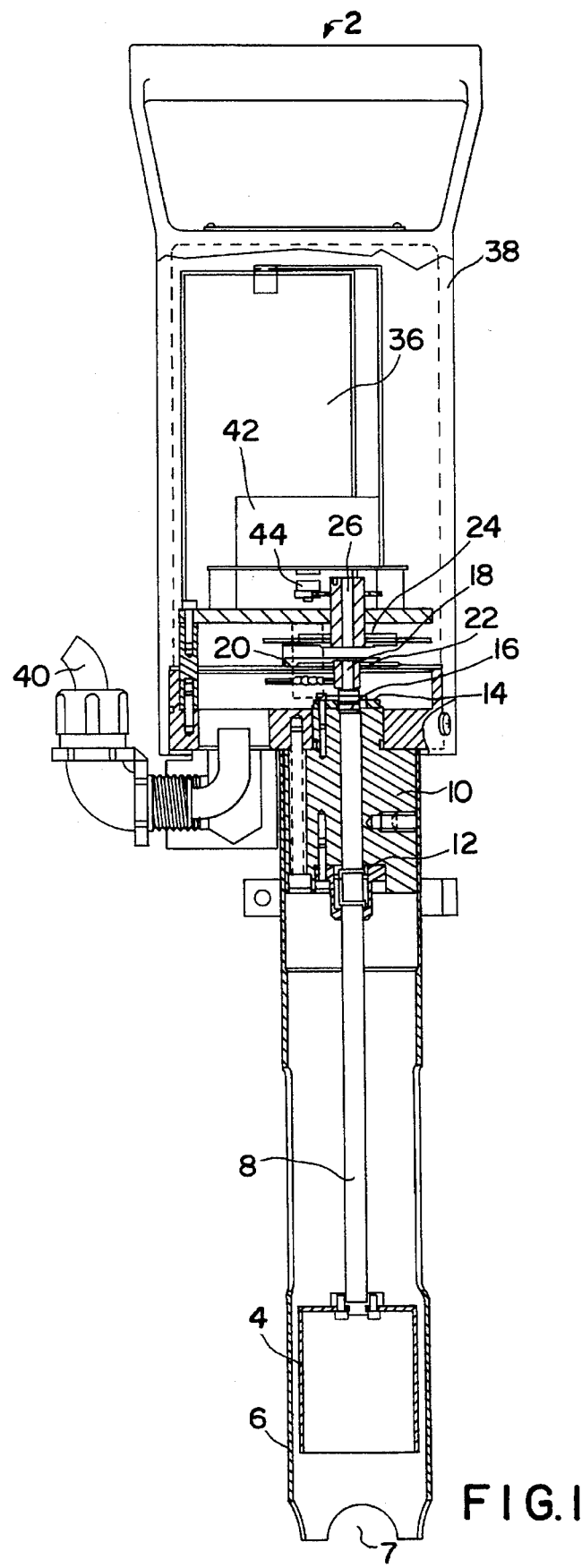
FIG. 1 is a cross-section view of a preferred embodiment of the invention.

FIG. 1 shows a viscometer 2 with a rotatable cylinder 4 enclosed in a tubular extension 6. The lower part of the extension is opened 7 for allowing the extension and cylinder to be immersed into a liquid—the liquid's viscosity to be measured. The cylinder 4 is coaxially supported from a 5/16" shaft 8. This shaft 8 is larger and made more rugged than shafts found in conventional laboratory viscometers. The shaft 8 extends through a housing 10 for about three inches. The clearance of the shaft to the through hole is about 0.003 inches. This tight shaft clearance impedes vapor penetration therethrough. The two collar ball-bearings assemblies 12 and 14 are shielded to further block such penetration. They radially align and maintain the shaft 8 within the through hole. The upper part of the shaft 8 has a radially extending collar assembly 16 that supports the shaft and cylinder on the upper bearing assembly 14. A 3/16 inch shaft 18 is fixed to the upper end of the shaft 8. This 3/16 shaft, and the transition between the 5/16 and the 3/16 does not contribute to misalignment since the ball bearings 12 and 14 control the alignment. The 3/16 inch shaft leads into a rotationally resilient member 24. The 3/16 is the standard size accommodated by the resilient member hub 20. The 3/16 shaft is inserted into the hub 20 and held by a set screw 22.

Figure 3:
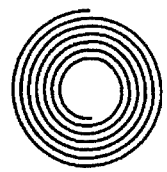
FIG. 2 and FIG. 3 are diagrams of springs.
Figure 2:
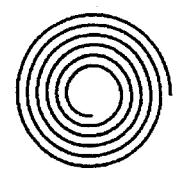

The rotationally resilient member 24 is preferably a spiral torque spring, shown in FIG. 2, with a torque of 56,000 dynes/cm, but other preferred embodiments include a 280,000 dyne-cm torque spring (cm being centimeter), shown in FIG. 3. FIGS. 2 and 3 show the spring configuration and are to the same approximate scale as the apparatus of FIG. 1. With these just described springs in place the bearings 12 and 14 are designed to contribute less than 1000 dyne-cm under normal use. Using these numbers the contribution of the bearings to the measured torque will be less than about 2% of full scale torque with the spring of FIG. 2 and less than ½% with the spring of FIG. 3.

Figure 4:
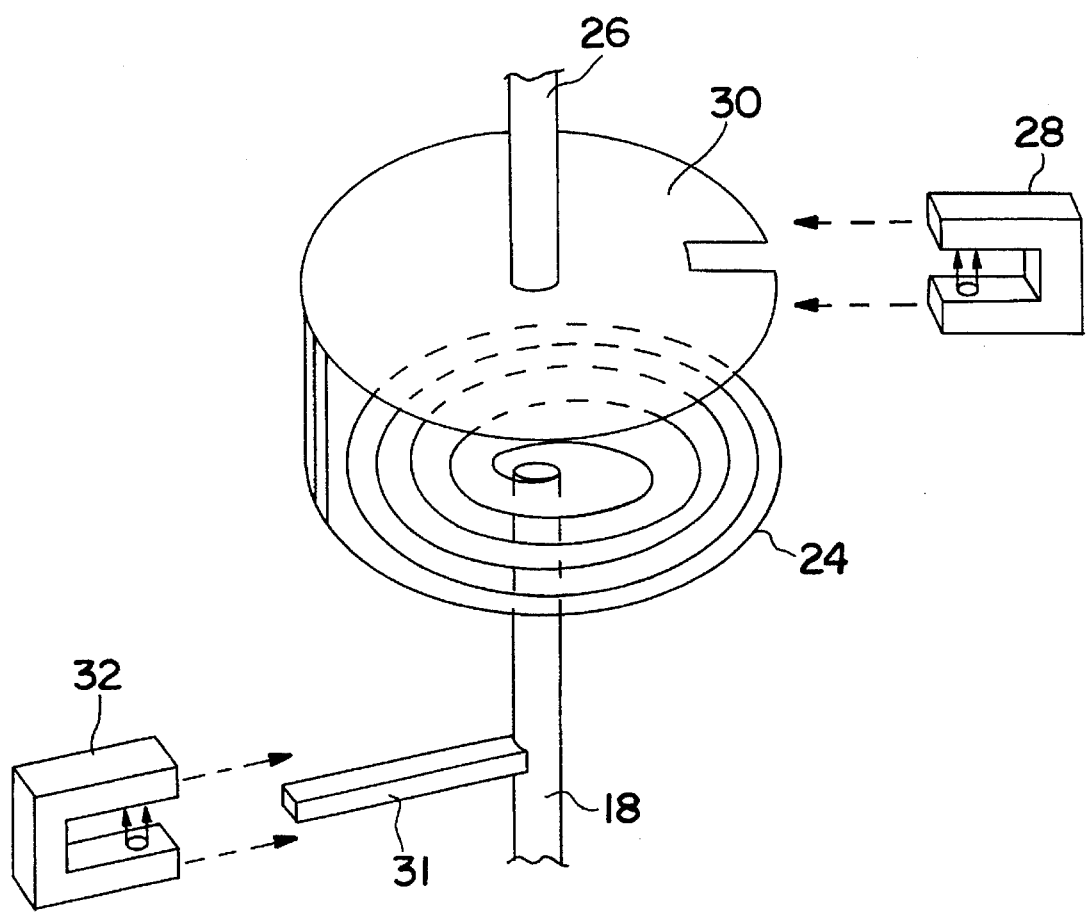
FIG. 4 is a pictorial of the sensing means arrangement for the spring deflections.

FIG. 4 is a pictorial representation of the resilient spring member with means to detect the deflection of the spring when measuring the viscosity of a liquid where the liquid causes a drag and deflection on the sensing shaft 18 relative to the driven shaft 26. A slotted wheel 30 radiates from driven shaft 26. An electro-optical sensor 28 is arranged such that the slot in wheel 30 passes between the arms of the electro-optical sensor 28. The sensor 28 is of a type including an LED (light emitting diode) and a photo sensitive element, usually a diode or transistor. Only when the slot passes between the arms of the sensor is light transmitted from the LED to the photosensitive element. In this manner the angular position of the slot, and thereby the driven shaft 26, is determined. An extension 31 radially emanates from the shaft 18 which is connected eventually to the cylinder 4. Another electro-optical sensor 32 is arranged such the extension 31 passes between the arms of this sensor thereby preventing light from the LED from hitting the photodetector. In this manner the angular position of the shaft 18, the sensing shaft, is determined. There is an initial offset between the two optical sensors when no liquid is being measured due to bearing torque on the spring causing a deflection in the spring. The initial offset and the deflection due to the bearings is the "zero" point. When a liquid is being measured there will always be, relative to the "zero", an additional torque and corresponding deflection of the spring. This deflection corresponds to the viscosity of the liquid. A slotted wheel can be used to replace the extension 31, but any combination of extensions and/or slotted wheels can be used in other preferred embodiments. In other preferred embodiments microswitches, magnetic pick-ups, transformer type pickups may be used instead of or in combination with optical sensors.

Referring back to FIG. 1, a printed circuit assembly 36 is mounted within the top housing 38 of the viscometer. The assembly 36 provides a DC voltage that powers electronic circuitry. A part of this circuitry includes signal conditioning electronics that drive the LEDs, and that accepts the output signals from the photo-sensitive elements. The printed circuit board also includes timing circuitry including a clock where the signals from the optical sensors are used to measure the added deflection of the spring. When the slotted wheel breaks the LED beam of device 28, that signal is used to begin counting clock signals, and when the extension 31 breaks the LED beams of device 32, the counting is stopped. The "zero" count is subtracted and the resulting count is a measure of the generated torque and consequently the viscosity of the liquid. This count is determined once for each revolution, although in other preferred embodiments additional pickups are used such that the count is determined several times during one revolution. The resetting of the clocks and other such operations are well known in the art. The resulting count is fed to an D to A converter (a digital to analog converter) of which many types are known in the art. In this preferred embodiment, a 12 bit converter is used. This converter is conditioned to output a 4 to 20 milliamperes signal that is a well known control signal. Other outputs, such as, 0 to 20 milliamperes, 1 to 5 milliamperes, or 0 to 1,5 or 10 volts or more, may also be generated. This output signal is fed external via the cable assembly 40. In preferred embodiments additional circuitry, namely an RC (resistor/capacitor) filter or other equivalent filters using inductors, active filters, or software filters can be used to smooth the output signal. Bouncing of the signal is especially obvious when the "zero" count is being established because the small bearing friction cannot overcome the mass spring bouncing which occurs due to slight irregularities in the drive. The filtering mitigates this bouncing.

Also on the printed circuit assembly a electric driver for the motor 42 is provided. In a preferred embodiment a 300 rpm synchronous motor is used, although other speed motors may be used. The motor output drives a gear reduction assembly 44. The output shaft of this gear reduction assembly is the shaft 26 that drives the spring. The gear reduction assembly also may be changed to yield different speeds. In this preferred embodiment a 300 rpm motor with a one to one gear reduction will drive the shaft 26 at 300 rpm. Higher speed give more frequent readouts but cause more wear on the bearings, and also cause the bearings to contribute more torque to the measurement. Although higher readings contribute to the "zero", which is later subtracted, there is a general problem since subtraction of a larger amount will cause the final readout to be somewhat less accurate and precise. In other preferred embodiments a gear reduction of ten to one is used resulting in a shaft 26 speed of 30 rpm. This arrangement gives fewer readouts per second, but also reduces the torque due to the bearings. Other gear reductions will give other speeds, but the above tradeoff persists.

In this preferred embodiment the housing is an explosion proof design. The housings are designed to provide a protection level to the NEC specifications for explosive gas environments.

In a preferred embodiment the motor 42 is typically approximately 1/50 hp, 300 rpm synchronous motor and drives a gear box with a reduction ratio of one to one up to ten to one, as described above. The 56,000 dyne-cm spring has a full scale deflection on the order of 120 to 240 degrees. In general, the larger the deflection, the more accurate the measurement.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A portable field viscometer comprising:

(a) a housing with a cylindrical extension, (b) a rotatable cylindrical spindle structure coaxially mounted within the cylindrical extension, where the space between the cylindrical extension and the cylindrical structure defines a volume filled with a liquid whose viscosity is being measured, (c) a first drive shaft for the cylindrical spindle with a first and second end, the first end coaxially connected to the cylindrical spindle structure, said second end held radially within the housing by two aligned and substantially axial spaced radial bearings and supporting the first drive shaft and cylindrical spindle structure with drag of less than 5% of the full scale torque range of said viscometer, (d) a rotationally resilient member connected to the second end of the first drive shaft, where the resilient member rotationally deflects responsive to the drag of said liquid sheared in said volume, and said rotationally resilient member provides substantially all the resistive torque to the viscous drag of the rotating cylinder structure, (e) means for rotationally driving the resilient member at 30–300 rpm, (f) means for reading the deflection of said resilient member, at least once per revolution and in the range of about 56,000 dynes/cm to about 280,000 dynes/cm, (g) means for measuring the deflection, and (h) means for calibrating said reading into at least a reading of torque or viscosity and (i) sealed enclosure means containing said means (e), (f), (g), (h).

2. A viscometer as defined in claim 1 wherein the rotationally resilient members and bearing are constructed and arranged so that the drag of axial spaced radial bearings contributes less than 1% of the full scale operating torque.

3. A viscometer as defined in claim 1 wherein the rotationally resilient member comprises a helix spring.

4. A viscometer as defined in claim 1 wherein the means for rotatably driving the rotationally resilient member comprises a motor driven second drive shaft connected to and driving the rotationally resilient member distal from the first drive shaft connection to the rotationally resilient member.

5. A viscometer as defined in claim 4 wherein the means for reading the deflection comprises:

a first radial extension emanating from the first drive shaft and rotating therewith, a second radial extension emanating from the second drive shaft and rotating therewith, a first means for sensing the rotation and position of the first radial extension, and a second means for sensing the rotation and position of the second radial extension.

6. A viscometer as defined in claim 5 wherein the means for reading the relative deflection between the first and the second radial extensions comprises an electronic clock and counter.

7. A viscometer as defined in claim 6 wherein the means for sensing said second extension provides a signal that starts the counter counting, and the means for sensing the first extension provides a signal that stops the counter, wherein the accumulated count in the counter is a measure of the relative angle between said second and first extensions.

8. A viscometer as defined in claim 1 further comprising an electronic means for outputting a 4 to 20 milliamperes signal in proportion to the measured deflection.

\* \* \* \* \*

UNITED STATES PATENT AND TRADEMARK OFFICE
CERTIFICATE OF CORRECTION

PATENT NO. : 5,503,003
DATED : April 2, 1996
INVENTOR(S) : David A. Brookfield

It is certified that error appears in the above-identified patent and that said Letters Patent is hereby corrected as shown below:

Item [57]

Please replace the original ABSTRACT with the following:

-- Viscometer with a rotating spindle (4) mounted on a shaft (8) supported via axially spaced, e.g. three inches, bearings (12,14) and driving a transducer rotary member via a stiff rotationally resilient member, the latter providing substantially all the resistive torque to viscous drag imparted to the spindle by an outer stationary member (6) when the spindle and stationary member are immersed in a liquid whose viscosity is to be measured, the viscometer being constructed with a handle (38) that encloses motor drive and electronic components of the viscometer, these features, as a whole, providing explosion protection and portability of the viscometer with sensitivity appropriate to portable usage.--

Signed and Sealed this

Twenty-third Day of July, 1996

Attest:

BRUCE LEHMAN

Attesting Officer          Commissioner of Patents and Trademarks